United States Patent [19]

Kaeding

[11] Patent Number: 4,477,585

[45] Date of Patent: Oct. 16, 1984

[54] PARA-SELECTIVE ZEOLITE CATALYSTS TREATED WITH CARBON DIOXIDE

[75] Inventor: Warren W. Kaeding, Westfield, N.J.

[73] Assignee: Mobil Oil Corporation, New York, N.Y.

[21] Appl. No.: 413,192

[22] Filed: Aug. 30, 1982

Related U.S. Application Data

[62] Division of Ser. No. 277,484, Jun. 26, 1981, Pat. No. 4,367,359.

[51] Int. Cl.$^3$ .................... B01J 29/06; B01J 29/28; B01J 27/14
[52] U.S. Cl. .................... 502/77; 502/60; 502/64; 502/71; 502/85
[58] Field of Search ............ 423/328; 252/443–445, 252/455, 437; 585/467, 485

[56] References Cited

U.S. PATENT DOCUMENTS

| | | | |
|---|---|---|---|
| 3,033,778 | 5/1962 | Frilette | 252/455 Z |
| 3,178,365 | 4/1965 | Miale | 208/120 |
| 3,375,064 | 3/1968 | Miale et al. | 252/455 Z |
| 3,444,097 | 5/1969 | Barclay | 252/455 Z |
| 3,702,886 | 11/1972 | Argaler et al. | 423/328 |
| 3,853,743 | 12/1974 | Schwartz | 208/111 |
| 4,002,698 | 1/1977 | Kaeding | 252/455 Z |
| 4,040,573 | 9/1977 | Kaeding | 252/432 |
| 4,098,837 | 7/1978 | Chu | 260/672 T |
| 4,137,195 | 1/1979 | Chu | 252/437 |
| 4,250,345 | 2/1981 | Chu | 585/467 |

FOREIGN PATENT DOCUMENTS 0012570 6/1980 European Pat. Off. .
2036709 12/1970 France .

OTHER PUBLICATIONS

Minachev et al., "Chemistry Reviews", vol. 2, 1980, pp. 1–44, 78 and 79.

Primary Examiner—Edward J. Meros
Attorney, Agent, or Firm—Alexander J. McKillop; Michael G. Gilman; Dennis P. Santini

[57] ABSTRACT

A process is provided for modifying ZSM-5 type zeolite catalysts with carbon dioxide treating agent in order to enhance the para-selective properties of such catalysts for the conversion of aromatic materials to dialkyl-substituted benzene compounds. Catalyst compositions so treated can be used in alkylation, transalkylation or disproportionation processes to provide product mixtures having exceptionally high concentrations of the para-dialkylbenzene isomer.

9 Claims, No Drawings

PARA-SELECTIVE ZEOLITE CATALYSTS TREATED WITH CARBON DIOXIDE

This is a division of application Ser. No. 277,484 filed June 26, 1981, now U.S. Pat. No. 4,367,359.

BACKGROUND OF THE INVENTION

1. Field of the Invention

The present invention relates to the preparation and use of modified zeolite catalyst compositions which are especially suitable for the conversion of substituted aromatic hydrocarbons to provide product mixtures enriched in the para-(or 1,4-) dialkyl substituted benzene isomer.

2. Description of the Prior Art

Production of dialkyl substituted benzene compounds via disproportionation, alkylation and/or transalkylation of aromatic hydrocarbons is an important step in a number of commercial chemical manufacturing processes. Such reactions can be carried out over a variety of catalyst materials. Alkylation of aromatic hydrocarbons utilizing crystalline aluminosilicate catalysts has, for example, been described. U.S. Pat. No. 2,904,607 to Mattox refers to alkylation of aromatic hydrocarbons with an olefin in the presence of a crystalline metallic aluminosilicate having uniform openings of about 6 to 15 Angstrom units. U.S. Pat. No. 3,251,897 to Wise describes alkylation of aromatic hydrocarbons in the presence of X or Y-type crystalline aluminosilicate zeolites, specifically such type zeolites wherein the cation is rare earth and/or hydrogen. U.S. Pat. No. 4,086,287 to Kaeding et al discloses the use of ZSM-5 type zeolites as catalysts for the alkylation of aromatic hydrocarbons such as toluene. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

The disproportionation of aromatic hydrocarbons in the presence of zeolite catalysts has been described by Grandio et al in the *Oil and Gas Journal*, Vol. 69, No. 48 (1971), U.S. Pat. Nos. 3,126,422; 3,413,374, 3,598,878; 3,598,879 and 3,607,961 show vapor-phase disproportionation of toluene over various catalysts.

In many of these prior art processes, the dialkylbenzene product produced contains more of the 1,3-isomer than either of the other two isomers. In the conventional methylation of toluene to form xylene, the product has the equilibrium composition of approximately 24 percent of 1,4-, 54 percent of 1,3- and 22 percent of 1,2-isomer. Of the dialkylbenzene isomers, 1,3-dialkylbenzene is often the least desired product, with 1,2- and 1,4-dialkylbenzene being the more useful products. 1,4-Dimethylbenzene, for example, is of particular value, being useful in the manufacture of terephthalic acid which is an intermediate in the manufacture of synthetic fibers such as "Dacron". Furthermore, 1,4- methylethylbenzene, i.e., para-ethyltoluene (PET), is useful for subsequent conversion to para-methylstyrene, and for this purpose ethyltoluene products containing as much as 97% of the para isomer are required.

Mixtures of dialkylbenzene isomers, either alone or in further admixture with ethylbenzene, have previously been separated by expensive superfractionation and multistage refrigeration steps. Such processes, as will be realized, involve high operation costs and have a limited yield. Alternatively, various modified zeolite catalysts have been developed to alkylate or disproportionate toluene with a greater or lesser degree of selectivity to 1,4-dialkylbenzene isomers. Hence, U.S. Pat. Nos. 3,972,832, 4,034,053, 4,128,592, and 4,137,195 disclose particular zeolite catalysts which have been treated with compounds of phosphorus and/or magnesium to increase para-selectivity of the catalysts. Para selective boron-containing zeolites are shown in U.S. Pat. No. 4,067,920 and para-selective, antimony-containing zeolites in U.S. Pat. No. 3,979,472. Similarly, U.S. Pat. Nos. 3,965,208 and 4,117,026 disclose other modified zeolites useful for shape selective reactions.

Notwithstanding the existence of such modified zeolite catalysts having para-selective properties, there is a continuing need to develop additional types of catalytic materials which are highly para-selective when used for the conversion of aromatic compounds to dialkylbenzene products. Accordingly, it is an object of the present invention to provide modified zeolite catalyst compositions which promote the conversion of aromatics to produce mixtures containing an exceptionally high percentage, e.g., 97% by weight or more, for alkylation of toluene, of para-dialkylbenzene isomer.

It is a further object of the present invention to provide such highly para-selective catalysts without necessarily resorting to expensive and/or time consuming catalyst selectivation techniques such as steaming and/or precoking after each instance of catalyst regeneration.

It is a further object of the present invention to provide highly para-selective alkylation, transalkylation and disproportionation processes employing the modified zeolite catalysts described herein.

SUMMARY OF THE INVENTION

The present invention relates to a process for modifying zeolite catalysts to render such catalysts highly para-selective for the conversion of aromatic compounds dialkyl substituted benzene compounds. The zeolite component of the catalysts so modified is one having a silica to alumina mole ratio of at least 12 and a constraint index within the approximate range of 1 to 12. Such zeolite catalysts are modified by treatment with carbon dioxide under catalyst treating conditions which enhance catalyst para-selectivity.

The present invention also relates to catalyst compositions modified in this manner and to alkylation, transalkylation and disproportionation processes utilizing such modified catalyst compositions.

DETAILED DESCRIPTION OF THE INVENTION

The crystalline zeolites used in the present invention are members of a particular class of zeolitic materials which exhibit unusual properties. Although these zeolites have unusually low alumina contents, i.e. high silica to alumina mole ratios, they are very active even when the silica to alumina mole ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

Zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN:(0–1.5)M$_{2/n}$O:(0–2)Al$_2$O$_3$:(100)SiO$_2$ wherein:
M is at least one cation having a valence n; and
RN is a C$_1$–C$_{20}$ organic compound having at least one amine functional group of pK$_a$ ≧ 7.

It is recognized that, particularly when the composition contains tetrahedral, framework aluminum, a fraction of the amine functional groups may be protonated. The doubly protonated form, in conventional notation, would be (RNH)$_2$O and is equivalent in stoichiometry to 2RN+H$_2$O.

The characteristic X-ray diffraction pattern of the synthetic zeolite ZSM-48 has the following significant lines:

| Characteristic Lines of ZSM-48 | |
| --- | --- |
| d(A) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/I$_o$, where I$_o$ is the intensity of the strongest line or peak, and d (obs.), the interplanar spacing in A, corresponding to the recorded lines, were calculated. In the foregoing table the relative intensities are given in terms of the symbols W=weak, VS=very strong and W-S=weak-to-strong. Ion exchange of the sodium with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | BROAD | PREFERRED |
| --- | --- | --- |
| Al$_2$O$_3$/SiO$_2$ = | 0 to 0.02 | 0 to 0.01 |
| Na/SiO$_2$ = | 0 to 2 | 0.1 to 1.0 |
| RN/SiO$_2$ = | 0.01 to 2.0 | 0.05 to 1.0 |
| OH$^-$/SiO$_2$ = | 0 to 0.25 | 0 to 0.1 |
| H$_2$O/SiO$_2$ = | 10 to 100 | 20 to 70 |
| H$^+$(added)/SiO$_2$ = | 0 to 0.2 | 0 to 0.05 | wherein RN is a C$_1$–C$_{20}$ organic compound having an amine functional group of pK$_a$ ≧ 7. The mixture is maintained at 80°–250° C. until crystals of the material are formed. H$^+$(added) is moles acid added in excess of the moles of hydroxide added. In calculating H$^+$(added) and OH values, the term acid (H$^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pK_a \geq 7$, as defined above, and includes such compounds as $C_3$–$C_{18}$ primary, secondary, and tertiary amines, cyclic amine (such as piperidine, pyrrolidine and piperazine), and polyamines such as $NH_2$-$C_nH_{2n}$-$NH_2$, wherein n is 4-12.

In all of the foregoing zeolites, the original cations can be subsequently replaced, at least in part, by calcination and/or ion exchange with another cation. Thus, the original cations can be exchanged into a hydrogen or hydrogen ion precursor form or a form in which the original cations have been replaced by a metal of, for example, Groups II through VIII of the Periodic Table. Thus, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |

|  | Void Volume | Framework Density |
|---|---|---|
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used as precursors to the alkaline-earth metal modified zeolites of the present invention. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing any given desired hydrocarbon conversion process including those of the present invention, it may be useful to incorporate the above-described crystalline zeolites with a matrix comprising another material resistant to the temperature and other conditions employed in the process. Such matrix material is useful as a binder and imparts greater resistance to the catalyst for the severe temperature, pressure and reactant feed stream velocity conditions encountered in, for example, many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

When the catalyst compositions of the type hereinbefore described are to be used for the conversion of aromatic compounds, the para-selective properties of such catalysts can preferably be enhanced in known manner by the treatment of such catalysts with oxides of a number of elements prior to treatment with carbon dioxide in accordance with the present invention. Most commonly such catalysts are treated with phosphorus and/or magnesium compounds in the manner described in U.S. Pat. Nos. 3,894,104; 4,049,573; 4,086,287; and 4,128,592, the disclosures of which are incorporated herein by reference.

Phosphorus, for example, can be incorporated into such zeolites in the form of phosphorus oxide in an amount of from about 0.25% to about 25% by weight of the catalyst composition. Such incorporation can be readily effected by contacting the zeolite composite with a solution of an appropriate phosphorus compound, followed by drying and calcining to convert the phosphorus compound to its oxide form.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphinite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain from one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products.

Particularly preferred are ammonium phosphates, including ammonium hydrogen phosphate, $(NH_4)_2HPO_4$, and ammonium dihydrogen phosphate, $NH_4H_2PO_4$.

Reaction of the zeolite with the phosphorus compound is effected by contacting the zeolite compound with such compound. Where the treating phosphorus compound is a liquid, such compound can be in a solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation is also preferred. The heating can be carried out in the presence of oxygen, for example, air. Heating can be at a temperature of about 150° C. However, higher temperatures, i.e., up to about 500° C. are preferred. Heating is generally carried out for 3-5 hours but may be extended to 24 hours or longer. While heating temperatures about about 500° C. can be employed, they are not necessary.

The amount of phosphorus incorporated with the zeolite should be at least about 0.25 percent by weight. However, it is preferred that the amount of phosphorus in the zeolite be at least about 2 percent by weight when the same is combined with a binder, e.g., 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction time, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite composite with the treating compound, and the amount and type of binder incorporated with the zeolite composite.

As noted, magnesium is another material commonly incorporated onto the zeolite composites of the present invention to thereby enhance their para-selectivity. Magnesium generally is incorporated as magnesium oxide and can be utilized either as the sole modifying agent or in combination with oxides of phosphorus as described hereinbefore or with other materials as described hereinafter. Incorporation of magnesium oxide is also effected by contacting the zeolite composite with a suitable compound of magnesium. Representative magnesium-containing compounds include magnesium acetate, magnesium nitrate, magnesium benzoate, magnesium propionate, magnesium 2-ethylhexanoate, magnesium carbonate, magnesium formate, magnesium oxylate, magnesium amide, magnesium bromide, magnesium hydride, magnesium lactate, magnesium laurate, magnesium oleate, magnesium palmitate, magnesium silicylate, magnesium stearate and magnesium sulfide.

Reaction of the zeolite composition with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e., may be used as a neat liquid. Where the treating compound is in the gaseous phase, it can be used by itself or can be used in admixture with a gaseous diluent relatively inert to the treating compound and the zeolite such as helium or nitrogen or with an organic solvent, such as octane or toluene.

Heating of the magnesium compound impregnated catalyst composition subsequent to preparation is preferred. The heating can be carried out in the same manner and to the same extent as descrieed hereinbefore with respect to incorporation of phosphorus. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g., 35 weight percent of alumina. The amount of magnesium oxide can be as high as about 25 percent by weight or more depending on the amount and type binder present. Preferably, the amount of magnesium oxide added to the zeolite is between about 1 and about 15 percent by weight.

The amount of magnesium oxide incorporated with the zeolite by reaction with the treating solution and subsequent calcination in air will depend on several factors. One of these is the reaction time, i.e., the time that the zeolite and the magnesium-containing source are maintained in contact with each other. With greater reactions times, all other factors being equal, a greater amount of magnesium oxide is incorporated with the zeolite. Other factors upon which the amount of magnesium oxide incorporated with the zeolite is dependent include reaction temperature, concentration of the treating compound in the reaction mixture, the degree to which the zeolite has been dried prior to reaction with the treating compound, the conditions of drying of the zeolite after reaction of the zeolite with the magnesium compound and the amount and type of binder incorporated with the zeolite.

In addition to treatment of the zeolite composites with phosphorus and/or magnesium as hereinbefore described, such zeolites may also be treated with a variety of other oxide materials to enhance para-selectivity. Such oxide materials include oxides of boron (U.S. Pat. No. 4,067,920); antimony (U.S. Pat. No. 3,979,472); beryllium (U.S. Pat. No. 4,260,843); Group VIIA metals (U.S. Pat. No. 4,275,256); alkaline earth metals (U.S. Pat. No. 4,288,647); Group IB metals (U.S. Pat. No. 4,276,438); Group VIB metals (U.S. Pat. No. 4,278,827); Group VIA metals (U.S. Pat. No. 4,259,537); Group IA elements (U.S. Pat. No. 4,329,533); cadmium (U.S. Ser. No. 139,611, filed Apr. 11, 1980 and now abandoned); iron and/or cobalt (U.S. Ser. No. 150,868, filed May 19, 1980 and now abandoned); Group IIIB metals (U.S. Pat. No. 4,276,437); Group IVA metals (U.S. Pat. No. 4,302,620); Group VA metals (U.S. Pat. No. 4,302,621); and Group IIIA elements (U.S. Pat. No. 4,302,622).

Treatment of the zeolite catalysts with any of the foregoing oxide materials to enhance para-selectivity will generally occur before such catalyst are treated with carbon dioxide in accordance with the present invention in order to provide even greater enhancement of the para-selective properties of such catalysts. Additional catalyst modifying procedures which may also optionally be employed to enhance catalyst para-selectivity include precoking and steaming, or combinations thereof.

Steaming entails contact of the zeolite with an atmosphere containing from about 5 to about 100 percent steam at a temperature of from about 250° C. to about 1000° C. for a period of between about 15 minutes and about 100 hours and under pressures ranging from subatmospheric to several hundred atmospheres. Preferably, steam treatment is effected at a temperature of between about 400° C. and about 700° C. for a period of between about 1 and about 24 hours.

Precoking of the catalyst serves to deposit a coating of between about 2 and about 75, and preferably between about 15 and about 75, weight percent of coke thereon to enhance catalyst selectivity. Precoking can be accomplished by contacting the catalyst with a hydrocarbon charge, e.g., toluene, under high severity conditions or alternatively at a reduced hydrogen to hydrocarbon relative concentration, i.e., 0 to 1 mole ratio of hydrogen to hydrocarbon, for a sufficient time to deposit the desired amount of coke thereon.

The zeolite catalyst composites described above, whether or not modified by treatment with phosphorus and/or magnesium oxides or other oxide materials, or modified by steaming or precoking techniques, are treated in accordance with the present invention with carbon dioxide to provide even further enhancement of the para-selective properties of the catalyst.

The catalysts described are treated with carbon dioxide under conditions which serve to enhance para-selectivity of the catalysts so treated. Catalyst treating conditions will vary with the concentration of the carbon dioxide treating agent employed. However, in general such para-selectivity enhancing catalyst treating conditions will include contact of the catalyst with a medium, preferably anhydrous, containing the $CO_2$ treating agent, at temperatures of from about 50° C. to 500° C. for a period of about 0.1 to 25 hours, followed by calcination of the treated catalyst at temperatures of from about 300° C. to 600° C.

The medium containing the carbon dioxide treating agent will generally will generally be gaseous and will contain from about 25% to 100% by volume of the $CO_2$ treating agent. Catalyst treatment operations may take place within the aromatics conversion reactor itself or may take place in a separate catalyst treatment vessel.

The treating medium is preferably passed over the catalyst at the rate of from about 20 to 100 cc/minute/gram catalyst at a temperature of from about 50° C. to 500° C. for a period of from about 0.25 to 3 hours.

It has been surprisingly discovered that treatment of the particular zeolite catalyst composites of this invention with the carbon dioxide treating agent in the manner herein described will provide catalysts having enhanced para-selective properties when used to promote the conversion of aromatic compounds to dialkyl substituted benzene compounds. Such enhancement occurs even with catalysts which are already highly para-selective by virtue of having been treated with, for example, phosphorus and/or magnesium compounds. Alternatively, treatment of the zeolite catalysts herein with the particular carbon dioxide treating agents of the present invention can permit elimination of the need for steaming and/or precoking procedures in order to reach given levels of para-selectivity, particularly after regeneration of such catalysts with air or other oxygen-containing gas.

The treated zeolite catalysts of the present invention are advantageously used to promote conversion of aromatic compounds to provide dialkyl-substituted benzene product mixtures which are highly enriched in the para-dialkyl substituted benzene isomer. Aromatic compound conversion of this type includes alkylation, transalkylation and disproportionation.

Alkylation of aromatic compounds in the presence of the above-described catalyst is effected by contact of the aromatic with an alkylating agent. A particularly preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C. At higher temperatures, the zeolites of high silica/alumina ratio are preferred. For example, ZSM-5 having a $SiO_2/Al_2O_3$ ratio of 30 and upwards is exceptionally stable at high temperatures. The reaction generally takes place at atmospheric pressure, but pressures within the approximate range of $10^5 N/m^2$ to $10^7 N/m^2$ (1-100 atmospheres) may be employed.

Some non-limiting examples of suitable alkylating agents would include olefins such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable aromatic hydrocarbon such as, for example, benzene, ethylbenzene, toluene, dimethylbenzene, diethylbenzene, methylethylbenzene, propylbenzene, isopropylbenzene, isopropylmethylbenzene, or substantially any mono- or di-substituted benzenes which are alkylatable in the 4-position of the aromatic ring.

The molar ratio of alkylating agent to aromatic compound is generally between about 0.05 and about 5. For instance, when methanol is employed as the methylating agent and toluene is the aromatic, a suitable molar ratio of methanol to toluene has been found to be approximately 0.1 to 1.0 mole of methanol per mole of toluene. When ethylene is employed as the alkylating agent and toluene is the aromatic, a suitable molar ratio of ethylene to toluene is approximately 0.05 to 2.5 moles of ethylene per mole of toluene.

Alkylation is suitably accomplished utilizing a feed weight hourly space velocity (WHSV) of between about 1 and about 1000, and preferably between about 1 and about 200. The reaction product, consisting predominantly of the 1,4-dialkyl isomer, e.g. 1,4-dimethylbenzene, 1-ethyl-4-methylbenzene, etc., or a mixture of the 1,4- and 1,3-isomers together with comparatively smaller amounts of 1,2-dialkylbenzene isomer, may be separated by any suitable means. Such means may include, for example, passing the reaction product stream through a water condenser and subsequently passing the organic phase through a column in which chromatographic separation of the aromatic isomers is accomplished. Alkylation using the carbon dioxide treated catalysts of the present invention can provide product mixtures containing at least 90% or even 95% or more by weight of the para-dialkylbenzene isomer.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene, ethyltoluene, and so forth.

Another process embodiment of this invention relates to the selective disproportionation of alkylated aromatic compounds to produce dialkylbenzenes wherein the yield of 1,4-dialkyl isomer is in excess of the normal equilibrium concentration. In this context, it should be noted that disproportionation is a special case of transalkylation in which the alkylatable hydrocarbon and the transalkylating agent are the same compound, for example when toluene serves as the donor and acceptor of a transferred methyl group to produce benzene and xylene.

The transalkylation and disproportionation reactions are carried out by contacting the reactants with the above described modified zeolite catalyst at a temperature of between about 250° C. and 750° C. at a pressure of between atmospheric ($10^5 N/m^2$) and about 100 atmospheres ($10^7 N/m^2$). The reactant feed WHSV will normally fall within the range of about 0.1 to about 50. Preferred alkylated aromatic compounds suitable for utilization in the disproportionation embodiment comprise toluene, ethylbenzene, propylbenzene or substantially any mono-substituted alkylbenzene. These aromatic compounds are selectively converted to, respectively, 1,4-dimethylbenzene, 1,4-diethylbenzene, 1,4-dipropylbenzene, or other 1,4-dialkylbenzene, as appropriate, with benzene being a primary side product in each instance. The product is recovered from the reactor effluent by conventional means, such as distillation, to remove the desired products of benzene and dialkylbenzene, and any unreacted aromatic component is recycled for further reaction.

The hydrocarbon conversion processes described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5–2%) is used to burn the coke in a controlled manner so as to limit the temperature to a maximum of around 500°–550° C.

The following examples will serve to illustrate certain specific embodiments of the hereindisclosed invention. These examples should not, however, be construed as limiting the scope of the invention, as there are many variations which may be made thereon without departing from the spirit of the disclosed invention, as those of skill in the art will recognize.

EXAMPLE I

A base catalyst composition was prepared for use in evaluating the carbon dioxide catalyst treating agent employed in this invention in comparison with known catalyst treating methods. To prepare such a base catalyst, HZSM-5 zeolite (60.5 grams) having a crystal size of about 2 microns in the form of 1/16 inch diameter extrudate with a 35 weight percent alumina binder was steamed at 600° C. for 1 hour. The steamed material was then impregnated with a solution of 38.7 grams of diammonium acid phosphate in 100 ml. of water, dried and calcined at 500° C. for about 2 hours in an open dish. The resulting product was cooled and impregnated with a solution of 195 grams of magnesium acetate tetrahydrate in 133 ml. of water, dried and calcined at 500° C. for about 16 hours. The final catalyst contained 4.93 weight percent magnesium, present as the oxide, and 3.48 weight percent phosphorus, present as the oxide.

EXAMPLE II

A procedure was established to evaluate various test catalysts, including the base catalyst of Example I, for their performance in catalyzing para-selective aromatic conversion reactions. In accordance with such a procedure, 2.2 grams of the test catalyst, 14–24 mesh, is centered in a quartz reactor. Low surface area quartz chips are used to position the catalyst and fill void spaces. After calcination with air at 500° C. for one hour, the temperature is adjusted to 425° C. Toluene is fed to the reactor at a rate of 8.8 cc/hr. with a WHSV of 3.5. A temperature rise occurs, and temperature is immediately adjusted to 450° C. After 25 minutes on stream at 450° C., the liquid product is collected for a period of 5 minutes, for analysis. A 2 cc gas sample is also taken at this time for analysis at a position just after the water condenser. The temperature is then increased rapidly and successively to 500° C., 550° C. and 600° C. In a similar manner, liquid and gaseous samples are taken for analysis at each temperature during the last five minutes of a 30-minute run. This series of tests is used to determine performance for selective toluene disproportionation to produce p-xylene and benzene.

The reactor is then purged with nitrogen (without regeneration) and the temperature adjusted to 375° C. Toluene is fed at a rate of 19.8 cc/hr, WHSV of 7.8, then ethylene is added at 15.6 cc/min., WHSV of 0.5, and the nitrogen purge is stopped. The temperature is rapidly adjusted to 400° C. In a similar manner, gaseous and liquid samples are taken during the last five minutes of a 30-minute run. An additional test run is made at 450° C. This series of tests is used to determine performance for the alklyation of toluene with ethylene to produce p-ethyltoluene.

Using these catalyst evaluation procedures, the base catalyst prepared as in Example I was tested for its performance in the toluene disproportionation and alkylation reactions described. Results for two runs are provided in Table I.

TABLE I

Para-Selectivity of Mg/P Treated ZSM-5 Base Catalyst

| REACTION | SELECTIVITY TO PARA-ISOMER (% by weight) | |
|---|---|---|
| | Run 1 | Run 2 |
| Toluene Disproportionation | | |
| 450° C. | 69.3 | 68.2 |
| 500° C. | 65.9 | 64.3 |
| 550° C. | 63.4 | 62.2 |
| 600° C. | 57.0 | 60.7 |
| Conversion Range: (% by wt.) | 1.1–11.0 | 1.1–12.7 |
| Toluene Alkylation w/Ethylene | | |
| 400° C. | 93.7 | 93.0 |
| 450° C. | 92.2 | 92.2 |
| Conversion Range: | 16.5–12.4 | 14.8–13.2 |

The Table I data illustrate that the Mg/P-treated base catalyst sample exhibits good para-selectivity which, unlike conversion, decreases with increase in temperature. In accordance with prior art procedures, such a catalyst can be coke selectivated to increase para-selectivity to levels of about 97% for toluene alkylation.

EXAMPLE III

To illustrate the catalyst treatment process of the present invention, the base catalyst as prepared in Example I is further treated by contact with carbon dioxide. Prior to conversion testing, anhydrous carbon dioxide is passed over the catalyst in the reactor at 100° C. for 15 minutes at the rate of about 50 cc/min/2.2 g catalyst. This is followed by a brief purge and then by calcination in air for 1 hour at 500° C. A similar treatment is given a second catalyst sample except that $CO_2$ contact is at 500° C. and lasts for 30 minutes. Catalyst samples so treated are then tested for their disproportionation and alkylation performance in the manner described in Example II. Results of such testing are provided in Table II.

TABLE II

Para-Selectivity of Mg/P ZSM-5 Catalyst Treated With Carbon Dioxide

| Treating Agent | $CO_2$ | $CO_2$ |
|---|---|---|
| Treating-Procedure | 15 min/100° C. | 30 min/500° C. |
| Run No. | 1 | 2 |
| TOL. DISPROPORT. | SELECTIVITY TO PARA ISOMER, WT % | |
| 450° C. | 78.0 | 79.2 |
| 500° C. | 78.6 | 79.6 |
| 550° C. | 74.0 | 74.7 |
| 600° C. | 73.5 | 74.7 |

TABLE II-continued

Para-Selectivity of Mg/P ZSM-5 Catalyst Treated With Carbon Dioxide

| Treating Agent | $CO_2$ | $CO_2$ |
|---|---|---|
| Treating-Procedure | 15 min/100° C. | 30 min/500° C. |
| Run No. | 1 | 2 |
| Conv. % | 0.8–12.1 | 0.8–11.9 |
| TOL + $C_2H_4$ | | |
| 400° C. | 95.8 | 96.2 |
| 450° C. | 94.7 | 95.2 |
| Conv. % | 14.6–12.6 | 15.4–12.8 |

The Table II data illustrate the increase in para-selectivity provided by treatment of the base catalyst with $CO_2$. Furthermore, it is evident that the decrease in para-selectivity with increased temperature was reduced significantly by $CO_2$ treatment.

What is claimed is:

1. A process for treating zeolite based catalysts, said catalysts comprising a crystalline zeolite material characterized by a silica to alumina ratio of at least 12 and a constraint index of from about 1 to 12 and from about 0.25% to 25% by weight of a modifying oxide selected from magnesium oxide, phosphorus oxide and mixtures of said oxides, said process comprising contacting said catalyst with a carbon dioxide treating agent under conditions capable of enhancing the para-selectivity of said catalysts in the conversion of aromatic compounds to dialkyl-substituted benzene compounds.

2. A process according to claim 1 wherein said para-selectivity enhancing conditions include contact of zeolite catalyst with treating agent at a temperature of from about 50° C. to 500° C. for a period of from about 0.1 to 25 hours, followed by calcination of the treated catalyst at a temperature of from about 300° C. to 600° C.

3. A process according to claim 2, wherein said zeolite is selected from ZSM-5, ZSM-11, ZSM-12, ZSM-23, ZSM-35, ZSM-38 and ZSM-48.

4. A process according to claim 2 wherein said carbon dioxide treating agent is provided in a treating medium comprising from about 25% to 100% by volume of said treating agent.

5. A process according to claim 4 wherein said treating medium is passed over said catalyst at the rate of from about 20 to 100 cc/min/gm catalyst at a temperature of from about 50° C. to 500° C. for a period of from about 0.25 to 3.0 hours.

6. A process according to claim 5 wherein said treating medium comprises 100% by volume of anhydrous $CO_2$.

7. A process according to claim 6 wherein said zeolite is ZSM-5.

8. A catalyst composition prepared in accordance with the process of claim 1, 2, 3, 4, 5, 6 or 7.

9. A catalyst composition according to claim 8 comprising from about 1 to 99% by weight of zeolite material with the balance of said composition comprising a binder for said zeolite material.

* * * * *

UNITED STATES PATENT AND TRADEMARK OFFICE
CERTIFICATE OF CORRECTION

PATENT NO. : 4,477,585
DATED : October 16, 1984
INVENTOR(S) : Warren W. Kaeding

It is certified that error appears in the above—identified patent and that said Letters Patent is hereby corrected as shown below:

Column 13, line 6, "Group VIB" should read --Group IVB--.

Signed and Sealed this

Ninth Day of April 1985

[SEAL]

Attest:

DONALD J. QUIGG

Attesting Officer     Acting Commissioner of Patents and Trademarks